(12) United States Patent
Baer-Beck et al.

(10) Patent No.: US 12,268,562 B2
(45) Date of Patent: Apr. 8, 2025

(54) METHOD FOR PROVIDING A CONFIGURATION INFORMATION FOR A LASER GUIDANCE SYSTEM

(71) Applicant: Siemens Healthineers AG, Forchheim (DE)

(72) Inventors: Matthias Baer-Beck, Spardorf (DE); Christian Hofmann, Erlangen (DE); Ferdinand Distler, Erlangen (DE); Volker That, Forchheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 378 days.

(21) Appl. No.: 17/953,741

(22) Filed: Sep. 27, 2022

(65) Prior Publication Data

US 2023/0101249 A1 Mar. 30, 2023

(30) Foreign Application Priority Data

Sep. 29, 2021 (EP) .................................. 21200001.2

(51) Int. Cl.
*A61B 90/13* (2016.01)
*A61B 6/08* (2006.01)
*A61B 90/00* (2016.01)

(52) U.S. Cl.
CPC ................ *A61B 90/13* (2016.02); *A61B 6/08* (2013.01); *A61B 90/361* (2016.02); *A61B 2090/3762* (2016.02)

(58) Field of Classification Search
CPC ............ A61B 1/00163; A61B 1/00165; A61B 1/00172; A61B 1/00174; A61B 1/00181;
(Continued)

(56) References Cited

U.S. PATENT DOCUMENTS

| 8,718,744 B2 | 5/2014 | Hannemann |
| 10,973,604 B2 | 4/2021 | Distler et al. |

(Continued)

FOREIGN PATENT DOCUMENTS

| CN | 106029000 A | * 10/2016 | ............. A61B 90/00 |
| DE | 102011004747 A1 | 8/2012 | |
| DE | 202020105594 U1 | 10/2020 | |

*Primary Examiner* — Don K Wong
(74) *Attorney, Agent, or Firm* — Harness, Dickey & Pierce, P.L.C.

(57) ABSTRACT

One or more example embodiments of the present invention relates in one aspect to a computer-implemented method for providing a configuration information for a laser guidance system for a medical intervention, comprising receiving laser projection data regarding a laser projection geometry of the laser guidance system; receiving 3D model data regarding a surface, the surface being located within an effective range of the laser guidance system; calculating shadowing data regarding a shadowing effect of the surface on the laser projection geometry based on the laser projection data and the 3D model data; selecting the configuration information based on the shadowing data, the configuration information being indicative of a configuration of the laser guidance system for visualizing a planned path of an instrument for the medical intervention; and providing the configuration information.

20 Claims, 3 Drawing Sheets

(58) Field of Classification Search
CPC ....... A61B 1/06; A61B 1/0605; A61B 1/0607; A61B 1/0615; A61B 17/3403; A61B 6/08
See application file for complete search history.

(56) References Cited

U.S. PATENT DOCUMENTS

| | | |
|---|---|---|
| 2012/0220863 A1 | 8/2012 | Hannemann |
| 2014/0107473 A1 | 4/2014 | Dumoulin et al. |
| 2018/0333208 A1 | 11/2018 | Kotian et al. |
| 2020/0057123 A1 | 2/2020 | Dumoulin et al. |
| 2020/0155111 A1 | 5/2020 | Nayak K et al. |
| 2021/0030512 A1 | 2/2021 | Distler et al. |

* cited by examiner

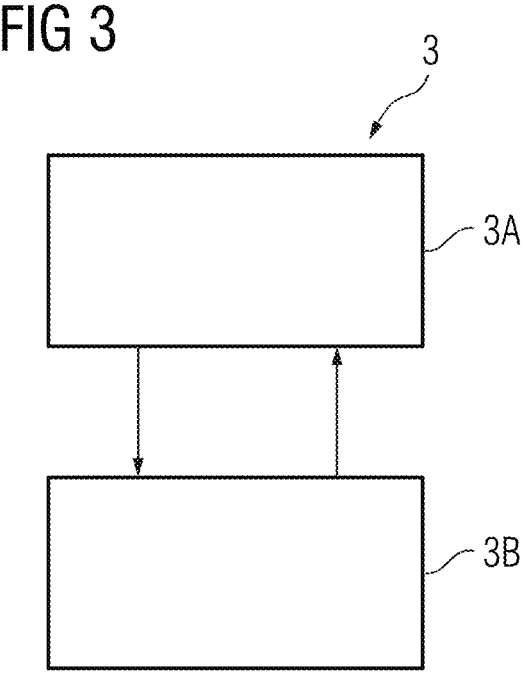

METHOD FOR PROVIDING A CONFIGURATION INFORMATION FOR A LASER GUIDANCE SYSTEM

CROSS-REFERENCE TO RELATED APPLICATION(S)

The present application claims priority under 35 U.S.C. § 119 to European Patent Application No. EP 21200001.2, filed Sep. 29, 2021, the entire contents of which are incorporated herein by reference.

BACKGROUND

Integrated Laser Guidance (ILG) is a laser projector-based approach to support medical personnel during an intervention, in particular during a computed tomography (CT) aided intervention. During the intervention, an instrument, for example, a needle, is inserted at a certain position and angle into the body of the patient. To avoid any harm to the patient the location and direction of the path of the instrument needs to be chosen carefully and the instrument needs to be inserted precisely at the chosen location and direction.

U.S. Pat. No. 8,718,744 B2 discloses an imaging medical apparatus with a device to identify a plane in space.

U.S. Pat. No. 10,973,604 B2 discloses a method is used to calibrate a light unit, including at least one light source, the light unit being part of a medical imaging apparatus.

The ILG system may comprise a plurality of laser projectors that are used to mark the designated location and direction of the planned path. The path planning can be done based on radiological image data, for example, from a prior planning scan. The planned path for the intervention can be visualized in form of an intersection line of two fan beams. Therefore, only two projectors selected from the plurality of laser projectors are used at the same time. A configuration of the laser guidance system for visualizing a given planned path can be selected, depending, for example, on the geometrical properties of the planned path.

SUMMARY

One or more example embodiments improve the selection of a configuration of a laser guidance system for visualizing a planned path. This problem is solved by subject matter claimed in at least the independent claims. Further advantageous embodiments and additional advantageous features are described in the dependent claims and in the specification.

One or more example embodiments of the present invention relates in one aspect to a computer-implemented method for providing a configuration information for a laser guidance system for a medical intervention, comprising receiving laser projection data regarding a laser projection geometry of the laser guidance system; receiving 3D model data regarding a surface, the surface being located within an effective range of the laser guidance system; calculating shadowing data regarding a shadowing effect of the surface on the laser projection geometry based on the laser projection data and the 3D model data; selecting the configuration information based on the shadowing data, the configuration information being indicative of a configuration of the laser guidance system for visualizing a planned path of an instrument for the medical intervention; and providing the configuration information.

According to one or more example embodiments, the laser projection geometry includes a plurality of candidate fan-beam pairs, each candidate fan-beam pair of the plurality of candidate fan-beam pairs comprises two candidate fan beams of the laser guidance system intersecting each other, the shadowing data comprises, for each candidate fan-beam pair of the plurality of candidate fan-beam pairs, a respective pair-specific shadowing information indicative of a shadowing effect of the surface on the respective candidate fan-beam pair, and the method further comprises selecting from the plurality of candidate fan-beam pairs based on the shadowing data to obtain a selected fan-beam pair, wherein the configuration information relates to the selected fan-beam pair for visualizing the planned path of the instrument for the medical intervention.

According to one or more example embodiments, intersection angle data are received, the intersection angle data comprises, for each candidate fan-beam pair of a subset of the plurality of candidate fan-beam pairs, an intersection angle information regarding an intersection angle of the two candidate fan beams of the respective candidate fan-beam pair, and the selecting from the plurality of candidate fan-beam pairs is further based on the intersection angle data.

According to one or more example embodiments, the laser guidance system comprises a plurality of laser projectors, and the configuration information is indicative of a first laser projector from the plurality of laser projectors and a second laser projector from the plurality of laser projectors for visualizing the planned path of the instrument in a form of an intersection line of a fan beam projected by the first laser projector and a fan beam projected by the second laser projector.

According to one or more example embodiments, the selected fan-beam pair consists of the fan beam projected by the first laser projector and the fan beam projected by the second laser projector.

According to one or more example embodiments, the 3D model data comprises a sequence of temporally successive 3D model data sets regarding the surface, and the configuration information is indicative of a sequence of temporally successive configurations of the laser guidance system.

According to one or more example embodiments, the method further includes receiving image data of a structure, the structure comprising the surface; and generating the 3D model data based on the image data of the structure.

According to one or more example embodiments, the image data of the structure comprises camera image data of the structure.

According to one or more example embodiments, the image data of the structure comprises radiological image data of the structure.

According to one or more example embodiments, the method further includes receiving virtual representation data regarding the structure, wherein the generating the 3D model data generates the 3D model data further based on the virtual representation data.

According to one or more example embodiments, the calculating the shadowing data calculates the shadowing data by applying a raytracing algorithm onto the laser projection data and the 3D model data.

According to one or more example embodiments, the method further includes operating the laser guidance system based on the configuration information to visualize the planned path of the instrument for the medical intervention.

According to one or more example embodiments, a data processing system includes a data interface; and a processor, the data processing system being configured to perform the method of claim 1.

According to one or more example embodiments, a medical imaging device includes the data processing system and the laser guidance system.

According to one or more example embodiments, the medical imaging device is a computed tomography device, and the laser guidance system is integrated into a gantry of the computed tomography device.

According to one or more example embodiments, a non-transitory computer-readable storage medium comprises instructions which, when the instructions are executed by a computer, cause the computer to perform a method according to one or more example embodiments.

BRIEF DESCRIPTION OF THE DRAWINGS

One or more example embodiments of the present invention will be illustrated below with reference to the accompanying figures using example embodiments. The illustration in the figures is schematic and highly simplified and not necessarily to scale.

FIG. 3 shows a data processing system according to at least one example embodiment.

DETAILED DESCRIPTION

Figure 1:
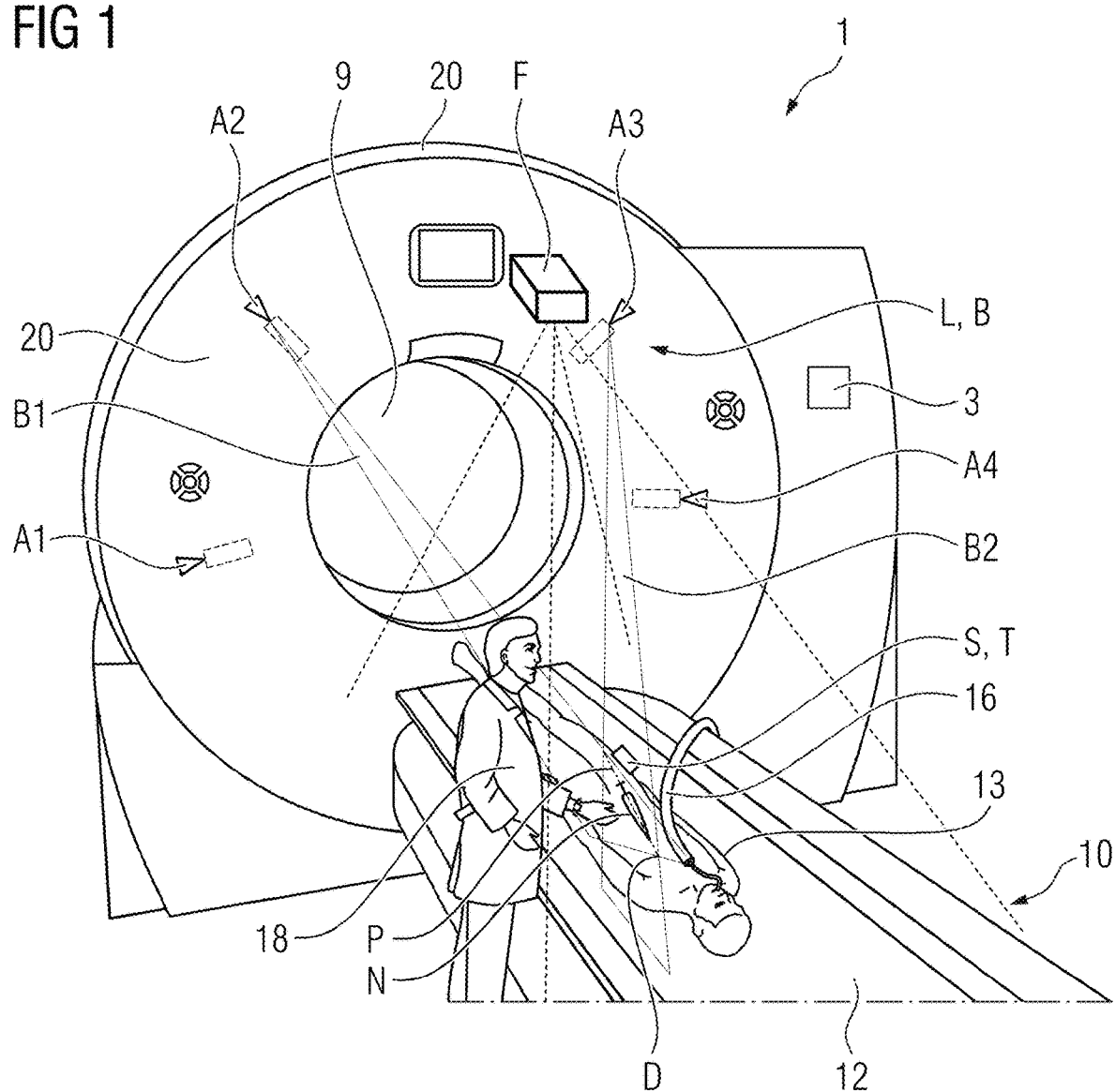
FIG. 1 shows a medical imaging device with a laser guidance system according to at least one example embodiment.

One or more example embodiments of the present invention relates in one aspect to a computer-implemented method for providing a configuration information for a laser guidance system for a medical intervention, the method comprising:

Receiving laser projection data regarding a laser projection geometry of the laser guidance system, Receiving 3D model data regarding a surface, the surface being located within an effective range of the laser guidance system, Calculating shadowing data regarding a shadowing effect of the surface on the laser projection geometry based on the laser projection data and the 3D model data, Selecting the configuration information based on the shadowing data, the configuration information being indicative of a configuration of the laser guidance system for visualizing a planned path of an instrument for the medical intervention, and Providing the configuration information.

Laser guidance systems for medical interventions are also known to the skilled person under the term "laser navigation system". The laser projection geometry may be adapted to the planned path and/or comprise one or more candidate laser projection geometries for visualizing the planned path.

The instrument may be, for example, a needle, in particular a biopsy needle, and/or a catheter. The surface may be, for example, a surface of a patient, a surface of a clinical user or a surface of a device. The 3D model data may relate to three spatial dimensions. The 3D model data may relate further to one temporal dimension. The 3D model data may be indicative of a position and/or an orientation of the surface relative to the laser guidance system.

The configuration information may be selected further based on the laser projection data. The configuration information may be indicative of a configuration of the laser guidance system, for which configuration a shadowing of those fan-beams that are used for visualizing the planned path, by the patient, the clinical staff or any other structures, e.g. immobilization devices, is avoided.

The shadowing data may be indicative of, for example, which part of the laser projection geometry is affected by the shadowing effect. The shadowing data may comprise binary information, indicating whether or not a given part of the laser projection geometry is affected by the shadowing effect. The shadowing data may comprise quantitative data regarding a degree of the shadowing effect and/or probability data regarding a risk for a given part of the laser projection geometry being affected by the shadowing effect, for example, during the medical intervention.

In another aspect, the laser projection geometry comprises a plurality of candidate fan-beam pairs, each candidate fan-beam pair of the plurality of candidate fan-beam pairs comprising two candidate fan beams, in particular planar candidate fan beams, of the laser guidance system intersecting each other, in particular intersection each other in a respective intersection line on which the planned path is located.

The shadowing data may comprise, for each candidate fan-beam pair of the plurality of candidate fan-beam pairs, a respective pair-specific shadowing information indicative of a shadowing effect of the surface on that candidate fan-beam pair. A selection from the plurality of candidate fan-beam pairs can be made based on the shadowing data, thereby obtaining a selected fan-beam pair. The configuration information may relate to the selected fan-beam pair for visualizing the planned path of the instrument for the medical intervention.

The shadowing data may be indicative of, for example, which candidate fan-beam pairs of the plurality of candidate fan-beam pairs are affected by the shadowing effect. The shadowing information may comprise binary information, indicating whether or not the candidate fan-beam pair is affected by the shadowing effect. The shadowing information may comprise quantitative information regarding a degree of the shadowing effect on that candidate fan-beam pair and/or probability information regarding a risk for the candidate fan-beam pair being affected by the shadowing effect, for example, during the medical intervention.

In another aspect, intersection angle data are received, the intersection angle data comprising, for each candidate fan-beam pair of a subset of the plurality of candidate fan-beam pairs, an intersection angle information regarding an intersection angle of the two candidate fan beams of that candidate fan-beam pair, wherein the selection from the plurality of candidate fan-beam pairs is made further based on the intersection angle data.

The intersection angle information regarding a given intersection angle may be, for example, a value of that intersection angle and/or an information whether the value of that intersection angle is within a predefined range. The intersection angle data may be calculated, for example, based on the laser projection data. The subset of the plurality of candidate fan-beam pairs may be identical to the plurality of candidate fan-beam pairs or may be a proper subset of the plurality of candidate fan-beam pairs. The candidate fan-beam pairs of the subset of the plurality of candidate fan-beam pairs may be selected from the plurality of candidate fan-beam pairs based on the shadowing data and/or the laser projection data.

Among the candidate fan-beam pairs that do not face any shadowing problems caused by the surface, the candidate fan-beam pair whose intersection angle fulfills a predefined criterion may be chosen for visualization of the planned path. For example, the candidate fan-beam pairs of the subset of the plurality of candidate fan-beam pairs may be compared with each other with regard to the respective intersection angle. The candidate fan-beam pair whose intersection angle is the one closest to 90° may be used for visualization. The reason for this criterion is that the visualization accuracy normally decreases as the intersection angle between the two laser planes departs from 90°. However, by relying solely on the intersection angle criterion, the influence of the geometry of the patient and other structures within the effective range of the laser guidance system would not be considered appropriately. These properties can be taken into account by selecting the configuration information based on the shadowing data.

The laser guidance system may comprise a plurality of laser projectors. The configuration information may be indicative of a first laser projector from the plurality of laser projectors and a second laser projector from the plurality of laser projectors for visualizing the planned path of the instrument in form of an intersection line of a fan beam projected by the first laser projector and a fan beam projected by the second laser projector.

Each of the projectors of the plurality of laser projectors may comprise, for example, a laser fan-beam source for emitting a laser fan-beam and two independent motors, one for rotating the laser fan-beam source itself and the other one for rotating an optical system, in particular a mirror, thereby rotating and moving the projected laser fan-beam.

The 3D model data can then be used, for example, to compute a respective shadowing effect for a given planned path for each of the available pairwise laser projector combinations.

In another aspect, the selected fan-beam pair consists of the fan beam projected by the first laser projector and the fan beam projected by the second laser projector.

The 3D model data may comprise a sequence of temporally successive 3D model data sets regarding the surface. The configuration information may be indicative of a sequence of temporally successive configurations of the laser guidance system, in particular in relation to the sequence of temporally successive 3D model data sets.

In another aspect, image data of a structure are received, the structure comprising the surface and/or the 3D model data are generated based on the image data of the structure.

The 3D model data of the surface can be computed based on the image data of the structure. Once the 3D model data have been generated, they can be used to determine shadowing effects for all available laser projector combinations.

The structure may be, for example, a structure of an object. The object may be, for example, a patient or a clinical user or a device. The structure of the patient or the clinical user may be, for example, a body part, in particular an arm, a hand, a torso or a head. The device may be, for example, an immobilization device, a reference frame, a robotic arm, an injector arm, a tablet holder, a tablet, a cable, a ventilation tube, an injection tube, a surgical drape or a radiation protection device.

In another aspect, the image data of the structure comprises camera image data of the structure, in particular 3D camera image data of the structure.

The camera image data may be acquired by a camera system, in particular by a 3D camera system. Based on the camera image data, the configuration of the laser guidance system may be adapted taking into account a movement of the structure relative to the laser guidance system, in particular a movement of the clinical staff in the scanning room. For example, if the clinical staff changes from one side of the patient to the other, this can be recorded successively in the camera image data, resulting in two different projector combinations being selected one after the other.

In another aspect, the image data of the structure comprises radiological image data of the structure.

The radiological image data may be acquired by a medical imaging device. The radiological image data may be, for example, computed tomography image data and/or magnetic resonance image data. Typically, before an interventional procedure a planning scan of the patient is done with a medical imaging device to plan the direction of the needle path. The planning scan may be, for example, a computed tomography scan and/or a magnetic resonance imaging scan.

The planning scan covers generally a much larger area then the subsequent radiological scans which are taken during the intervention to control the direction of the needle path, but the positioning of the patient is as close as possible to the position during the procedure. Besides the needle path planning the initial radiological scan can also be used to generate a 3D model of the patient surface and potential other structures which are placed close to the patient, for example, immobilization devices.

Using the camera image data and the radiological image data simultaneously for generating the 3D model data may be advantageous for several reasons.

The camera system itself may be exposed to shadowing problems since some regions of the patient surface may be shadowed from the camera system by the patient itself. In particular, lateral regions of the patient surface may be shadowed by the patient itself from a camera that is looking at a frontal plane of the patient. This could be the case, for example, when the camera system is looking at a patient from the ceiling of the scanning room, the patient being positioned in supine position. This may be a limiting factor for computing shadowing effects on fan beams that are directed essentially perpendicular to an optical axis of the camera. On the other hand the radiological image data are not affected by such effects and a 3D model of all regions of the scanned patient surface can be computed without major issues.

Since the radiological image data is typically acquired only once before the actual intervention procedure, the situation during the planning scan could be different from the situation during the actual interventional procedure. Based on the camera image data, the influence of the clinical staff (radiologists, techs, etc.) which are in the scanning room during the actual interventional procedure, for example, to puncture a needle into the patient, may be incorporated into the computation of the shadowing effects.

Furthermore, the range of the planning scan is typically chosen as low as reasonable possible to reduce the overall dose to the patient. While the range of the planning scan is chosen large enough to cover all regions needed to plan the intervention, it may lack some coverage that is needed to compute the shadowing effects. This may be compensated by using additionally the information form a camera system where such dose related limitations do not apply.

Therefore, based on the radiological image data, the lateral shape of the patient contour can be taken into account, while the camera image data can be used to adapt the configuration of the laser guidance system to a given scene in the scanning room, in particular regarding movements of clinical staff, and/or to enlarge the area that can be taken into account for the computation of shadowing effects.

In another aspect, virtual representation data regarding the structure are received, wherein the 3D model data are further generated based on the virtual representation data.

The virtual representation data may be, for example, a digital twin of the structure and/or a virtual avatar of the structure. The virtual representation data may be complemented and/or adjusted based on the image data of the structure, in particular based on the camera image data of the structure and/or the radiological image data of the structure. The virtual representation data regarding the structure of a patient may comprise, in particular, virtual patient information.

In another aspect, the shadowing data are calculated by applying a raytracing algorithm onto the laser projection data and the 3D model data. For example, an image analysis algorithm may be applied onto an output of the raytracing algorithm, thereby obtaining the shadowing data, in particular the shadowing data that comprise the binary data, the quantitative data and/or the probability data.

The image analysis algorithm may be a trained machine learning algorithm. The trained machine learning algorithm can be based on one or more of the following architectures: convolutional neural network, deep belief network, random forest, deep residual learning, deep reinforcement learning, recurrent neural network, Siamese network, generative adversarial network or auto-encoder. In particular, the trained machine learning algorithm can be embodied as a deep learning algorithm, in particular as a deep convolutional neural network.

The laser guidance system may be operated based on the configuration information to visualize the planned path of the instrument for the medical intervention.

Thus, the planned path of the instrument for the medical intervention can be visualized based on the configuration of the laser guidance system, in particular, in form of an intersection line of the two fan-beams of the selected fan-beam pair. One fan-beam of the selected fan-beam pairs may be projected by the first laser projector from the plurality of laser projectors and the other fan-beam of the selected fan-beam pairs may be projected by the second laser projector from the plurality of laser projectors.

One or more example embodiments of the present invention relates in one further aspect to a data processing system, comprising a data interface and a processor, the data processing system being configured for carrying out the method according to one of the aspects of one or more example embodiments of the present invention.

One or more example embodiments of the present invention relates in one further aspect to a medical imaging device comprising the data processing system and the laser guidance system.

The laser guidance system may be integrated into a gantry of the medical imaging device. The medical imaging device may further comprise the camera system, in particular the 3D camera system, for acquiring the camera image data. The camera system may comprise a camera that is integrated into a gantry of the medical imaging device and/or a camera that is mounted separately from a gantry of the medical imaging device, for example, on a room ceiling. The medical imaging device may be configured for acquiring the radiological image data.

The medical imaging device may comprise a patient bed with a bed board for accommodating a patient, the bed board being mounted so that its position and/or orientation relative to the laser guidance system can be changed, for example, through a translation along a horizontal longitudinal direction of the bed board and/or along a vertical direction and/or through a rotation around a horizontal longitudinal direction of the bed board and/or around a vertical direction.

The configuration information may be further indicative of a configuration of the medical imaging device, in particular indicative of a configuration information of the patient bed. The configuration information may be further indicative, for example, of a change of a position and/or an orientation of the bed board relative to the laser guidance system to reduce, in particular to eliminate, the shadow effect.

One or more example embodiments of the present invention relates in one further aspect to a computer program product or a computer-readable storage medium, comprising instructions which, when the instructions are executed by a computer, cause the computer to carry out the method according to one of the aspects of one or more example embodiments of the present invention.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable storage medium can be embodied as non-permanent main memory (e.g. random-access memory) or as permanent mass storage (e.g. hard disk, USB stick, SD card, solid state disk).

The data processing system can comprise, for example, at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Data processing for performing an action of a method may be carried out in the processor.

Data, in particular each of the laser projection data, the 3D model data, the intersection angle data, the image data and the virtual representation data, can be received, for example, by receiving a signal that carries the data and/or by reading the data from a computer memory. Data, in particular the configuration information, can be provided, for example, by transmitting a signal that carries the data and/or by writing the data into a computer memory and/or by displaying the data on a display.

In the context of the present invention, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described systems are merely preferred example embodiments of the invention, and that the invention can be varied by a person skilled in the art, without departing from the scope of the invention as it is specified by the claims.

FIG. 1 shows the medical imaging device 1 in form of a computed tomography device, comprising the gantry 20, the patient bed 10, the laser guidance system L, the camera system F and the data processing system 3. The laser guidance system L is integrated into the gantry 20 and comprises a plurality of laser projectors A1, A2, A3 and A4. Each of the laser projectors A1, A2, A3 and A4 is configured for projecting a planar laser fan beam.

The planned path P for the instrument N touches the surface of the patient 13 at point D and is visualized in form of an intersection line of the fan beam B1 projected by the first laser projector A2 and the fan beam B2 projected by the second laser projector A3. Other typical pairwise projector combinations that can be used for needle path display are, for example, a combination of the laser projectors A1 and A2 and a combination of the laser projectors A3 and A4. The clinical user 18 and the device 16 in form of a ventilation tube are located within the effective range of the laser guidance system L.

The patient bed 10 comprises the bed board 12 for accommodating the patient 13, the bed board 12 being mounted so that its position and/or orientation relative to the gantry 20 can be changed, for example, for inserting the patient 13 into the opening 9 of the gantry 20, in particular along a horizontal longitudinal direction of the bed board 12, and/or for adjusting the position of the bed board 12 along a vertical direction. This could be used also for changing the position and/or orientation of the bed board 12 relative to the laser guidance system L.

Figure 2:
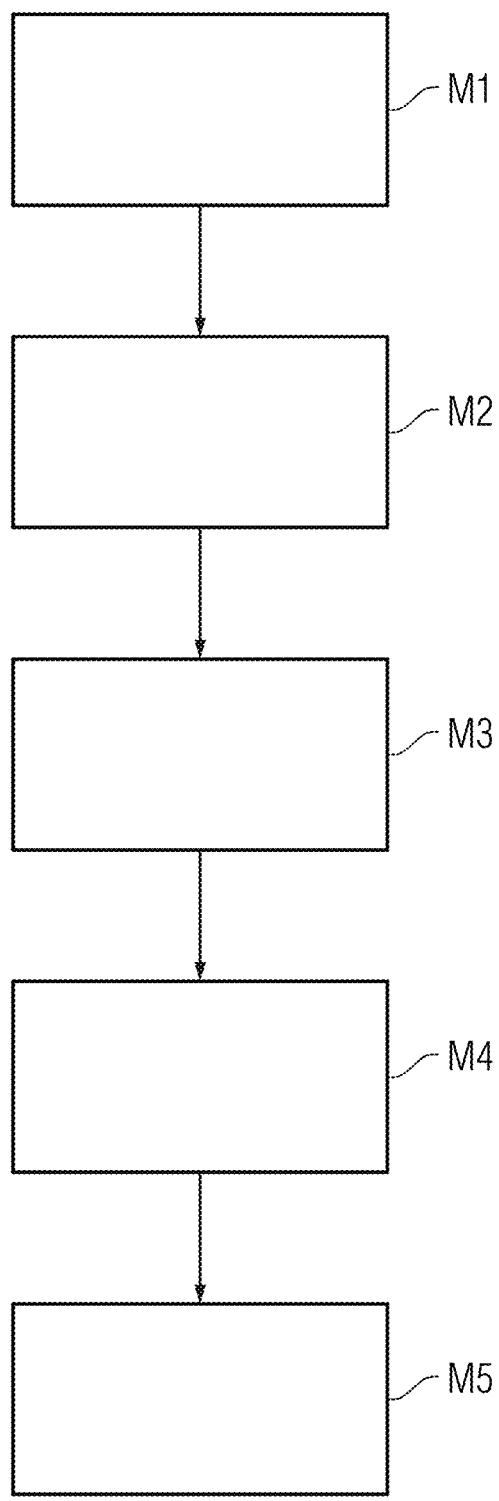
FIG. 2 shows a flow chart for a method for providing configuration information for a laser guidance system for a medical intervention according to at least one example embodiment.

FIG. 2 shows a flow chart for a method for providing a configuration information for a laser guidance system L for a medical intervention, the method comprising:

Receiving M1 laser projection data regarding a laser projection geometry B of the laser guidance system L, Receiving M2 3D model data regarding a surface S, the surface S being located within an effective range of the laser guidance system L, Calculating M3 shadowing data regarding a shadowing effect of the surface S on the laser projection geometry B based on the laser projection data and the 3D model data, Selecting M4 the configuration information based on the shadowing data, the configuration information being indicative of a configuration of the laser guidance system L for visualizing a planned path P of an instrument N for the medical intervention, and Providing M5 the configuration information.

The configuration information is indicative of the first laser projector A2 from the plurality of laser projectors and the second laser projector A3 from the plurality of laser projectors for visualizing the planned path P of the instrument N in form of an intersection line of the fan beam B1 projected by the first laser projector A2 and the fan beam B2 projected by the second laser projector A3. The selected fan-beam pair consists of the fan beam B1 projected by the first laser projector A2 and the fan beam B2 projected by the second laser projector A3.

Image data of the structure T are received, the structure T comprising the surface S. The 3D model data are generated based on the image data of the structure T. The image data of the structure T comprise camera image data of the structure T. The camera image data of the structure T are acquired by the camera system F. The image data of the structure T further comprise radiological image data of the structure T. The radiological image data of the structure T have been acquired in a planning scan by the medical imaging device 1.

The laser guidance system L is operated based on the configuration information to visualize the planned path P of the instrument N for the medical intervention.

FIG. 3 shows a data processing system 3, comprising a data interface 3A and a processor 3B, the data processing system 3 being configured for carrying out a method as described with respect to FIG. 2. More specifically, the data interface 3A may provide the receiving and obtaining of data explained herein. The processor 3B executes instructions, stored internally or externally, to cause the data processing system 3 to perform the method of FIG. 2.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

We claim:

1. A computer-implemented method for providing a configuration information for a laser guidance system for a medical intervention, the method comprising:
    receiving laser projection data regarding a laser projection geometry of the laser guidance system;
    receiving 3D model data regarding a surface, the surface being located within an effective range of the laser guidance system;
    calculating shadowing data regarding a shadowing effect of the surface on the laser projection geometry based on the laser projection data and the 3D model data;
    selecting the configuration information based on the shadowing data, the configuration information being indicative of a configuration of the laser guidance system for visualizing a planned path of an instrument for the medical intervention; and
    providing the configuration information.

2. The method of claim 1, wherein the laser projection geometry includes a plurality of candidate fan-beam pairs, each candidate fan-beam pair of the plurality of candidate fan-beam pairs comprises two candidate fan beams of the laser guidance system intersecting each other, the shadowing data comprises, for each candidate fan-beam pair of the plurality of candidate fan-beam pairs, a respective pair-specific shadowing information indicative of a shadowing effect of the surface on the respective candidate fan-beam pair, and the method further comprises:
    selecting from the plurality of candidate fan-beam pairs based on the shadowing data to obtain a selected fan-beam pair,
    wherein the configuration information relates to the selected fan-beam pair for visualizing the planned path of the instrument for the medical intervention.

3. The method of claim 2, wherein intersection angle data are received, the intersection angle data comprises, for each candidate fan-beam pair of a subset of the plurality of candidate fan-beam pairs, an intersection angle information regarding an intersection angle of the two candidate fan beams of the respective candidate fan-beam pair, and the selecting from the plurality of candidate fan-beam pairs is further based on the intersection angle data.

4. The method of claim 2, wherein
the laser guidance system comprises a plurality of laser projectors, and
the configuration information is indicative of a first laser projector from the plurality of laser projectors and a second laser projector from the plurality of laser projectors for visualizing the planned path of the instrument in a form of an intersection line of a fan beam projected by the first laser projector and a fan beam projected by the second laser projector.

5. The method of claim 4, wherein the selected fan-beam pair consists of the fan beam projected by the first laser projector and the fan beam projected by the second laser projector.

6. The method of claim 1, wherein
the 3D model data comprises a sequence of temporally successive 3D model data sets regarding the surface, and
the configuration information is indicative of a sequence of temporally successive configurations of the laser guidance system.

7. The method of claim 1, further comprising:
receiving image data of a structure, the structure comprising the surface; and
generating the 3D model data based on the image data of the structure.

8. The method of claim 7, wherein the image data of the structure comprises camera image data of the structure.

9. The method of claim 7, wherein the image data of the structure comprises radiological image data of the structure.

10. The method of claim 7, further comprising:
receiving virtual representation data regarding the structure, wherein the generating the 3D model data generates the 3D model data further based on the virtual representation data.

11. The method of claim 1, wherein the calculating the shadowing data calculates the shadowing data by applying a raytracing algorithm onto the laser projection data and the 3D model data.

12. The method of claim 1, further comprising:
operating the laser guidance system based on the configuration information to visualize the planned path of the instrument for the medical intervention.

13. A data processing system, comprising:
a data interface; and
a processor, the data processing system being configured to perform the method of claim 1.

14. A medical imaging device comprising the data processing system of claim 13 and the laser guidance system.

15. The medical imaging device of claim 14, wherein
the medical imaging device is a computed tomography device, and
the laser guidance system is integrated into a gantry of the computed tomography device.

16. A non-transitory computer-readable storage medium comprising instructions which, when the instructions are executed by a computer, cause the computer to perform the method of claim 1.

17. The method of claim 1, wherein
the laser guidance system comprises a plurality of laser projectors, and
the configuration information is indicative of a first laser projector from the plurality of laser projectors and a second laser projector from the plurality of laser projectors for visualizing the planned path of the instrument in a form of an intersection line of a fan beam projected by the first laser projector and a fan beam projected by the second laser projector.

18. The method of claim 5, wherein
the 3D model data comprises a sequence of temporally successive 3D model data sets regarding the surface, and
the configuration information is indicative of a sequence of temporally successive configurations of the laser guidance system.

19. The method of claim 6, further comprising:
receiving image data of a structure, the structure comprising the surface; and
generating the 3D model data based on the image data of the structure.

20. The method of claim 10, wherein the calculating the shadowing data calculates the shadowing data by applying a raytracing algorithm onto the laser projection data and the 3D model data.

* * * * *